(12) United States Patent
Cohen (10) Patent No.: US 7,177,705 B2
(45) Date of Patent: *Feb. 13, 2007

(54) SURFACE ELECTRODE FOR ELECTRICAL STIMULATION OF TISSUE

(75) Inventor: Shlomi Cohen, Tel-Aviv (IL)

(73) Assignee: Stimu-Heal Inc., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/893,240

(22) Filed: Jul. 19, 2004

(65) Prior Publication Data

US 2004/0249432 A1    Dec. 9, 2004

Related U.S. Application Data

(63) Continuation-in-part of application No. 10/367,920, filed on Feb. 19, 2003, now Pat. No. 7,043,308.

(51) Int. Cl.
*A61N 1/04* (2006.01)

(52) U.S. Cl. ................ 607/152; 607/142; 607/149

(58) Field of Classification Search ............. 607/115, 607/144, 149, 152–153, 142
See application file for complete search history.

(56) References Cited

U.S. PATENT DOCUMENTS

| | | | |
|---|---|---|---|
| 4,300,575 A | | 11/1981 | Wilson |
| 4,367,755 A | | 1/1983 | Bailey |
| 4,559,950 A | | 12/1985 | Vaughan et al. |
| 4,699,146 A | * | 10/1987 | Sieverding .......... 600/391 |
| 4,767,401 A | * | 8/1988 | Seiderman .......... 604/20 |
| 4,787,390 A | * | 11/1988 | Takata ............... 600/396 |
| 4,937,323 A | | 6/1990 | Silver et al. |
| 5,309,909 A | | 5/1994 | Gadsby et al. |
| 5,520,180 A | * | 5/1996 | Uy et al. ............ 600/397 |
| 5,824,033 A | * | 10/1998 | Ferrari .............. 607/142 |
| 5,974,344 A | * | 10/1999 | Shoemaker, II ...... 607/149 |
| 6,039,760 A | * | 3/2000 | Eisenberg ........... 623/15.12 |
| 6,115,625 A | * | 9/2000 | Heard et al. ........ 600/391 |

(Continued)

FOREIGN PATENT DOCUMENTS

GB         1328111        8/1973

(Continued)

OTHER PUBLICATIONS

Satterfield "Heterogeneous Catalysis in Practice" McGraw-Hill Inc, 1980, p. 336.

*Primary Examiner*—Robert E. Pezzuto
*Assistant Examiner*—Jessica L. Reidel
(74) *Attorney, Agent, or Firm*—Mark M. Friedman (57) ABSTRACT

A surface electrode for long-term electrical communication with a skin surface of a patient, the surface electrode including: (a) a highly-conductive foil, for operatively connecting to a power source, for communication of an electrical signal between the highly-conductive foil and the skin surface of the patient, and (b) a securing arrangement for securing the highly-conductive foil to the skin surface, wherein the foil has a plurality of macroscopic air-permeable regions for fluid communication of air with the skin surface, and wherein the plurality of macroscopic air-permeable regions has a first surface area, the foil has a second surface area, and a ratio of the first surface area to the second surface area is at least 0.1.

32 Claims, 4 Drawing Sheets

U.S. PATENT DOCUMENTS

| | | |
|---|---|---|
| 6,121,508 A | 9/2000 | Bischof et al. |
| 6,135,953 A | 10/2000 | Carim |
| 7,043,308 B2 * | 5/2006 | Cohen ........................ 607/152 |
| 2002/0117408 A1 | 8/2002 | Solosko et al. |

FOREIGN PATENT DOCUMENTS

| | | |
|---|---|---|
| WO | WO01/48111 | 7/2001 |
| WO | WO02/098502 | 12/2002 |

* cited by examiner

FIG. 1A

PRIOR ART

PRIOR ART

PRIOR ART

Fig 4

SURFACE ELECTRODE FOR ELECTRICAL STIMULATION OF TISSUE

This is a continuation-in-part (CIP) of U.S. patent application Ser. No. 10/367,920, filed Feb. 19, 2003, now U.S. Pat. No. 7,043,308.

FIELD AND BACKGROUND OF THE INVENTION

The present invention relates to a surface electrode for transcutaneous electrical communication, and, in particular, to a surface electrode providing sustained mechanical and electrical performance over long-term use, especially for use underneath a cast on the limb of a patient.

Electrodes which are used to deliver electrical stimulation through the surface of the skin generally require the use of a conductive liquid or solid gel, often termed "hydrogel", to provide a continuous conductive path between the skin and the current source. Conductive gels contain a salt (typically KCl or NaCl) in order to achieve the requisite electrical current flow. The preferred gel is one with a high salt content, since such a gel produces a better conductor than that obtained when using a gel with a low salt content. In addition, the use of a high salt content gel typically requires less skin abrasion at the time of application to reduce the impedance of the skin-electrode interface after subsequent electrode application.

For ease of use, it is often desirable to apply the conductive liquid or solid gel at the point of manufacture, creating a "pre-gelled" electrode. U.S. Pat. No. 4,559,950 to Vaughn and U.S. Pat. No. 5,309,909 to Gadsby describe such electrodes. Pre-gelled electrodes save the step of manually applying the gel to the electrode at the time of electrode application and speed the application process considerably.

Known gels are typically hydrophilic, to improve conductivity of the gel, and perhaps more importantly, to slow the gradual dehydration of stored, sealed electrodes. It is reported by United States Patent Application No. 20020117408 to Solosko, et al., that the shelf life of an electrode pad is largely determined by the length of time it takes for enough water moisture to evaporate out of the hydrogel and escape the package of the pad. It is further articulated that as moisture escapes from the packaging, the electrical properties of the electrode pads become increasingly compromised.

This problem is a critical one for numerous and varied medical applications. For example, when electrode pads are utilized with a defibrillator, a very significant factor includes changes in small and large signal impedance values between a patient and a defibrillator. As the hydrogel dries out, the impedance values increase, making it more difficult to monitor electrical signals from the patient, obtain transthoracic impedance, and deliver energy into the body.

Water loss can affect the mechanical properties of the hydrogel as well. In some hydrogels, the loss of water causes the hydrogel to skin over or solidify, especially around the edges, which inhibits the ability of the hydrogel to adhere to the skin. This partial or complete loss of adhesion can render an electrode useless since it cannot then create or maintain an effective contact with the patient's skin. Thus, water loss from the electrode pad can prevent or attenuate receipt of electrocardiogram (ECG) signals by a defibrillator. In addition, water loss from the electrode pad can alter the delivery of defibrillation energy from a defibrillator to the patient.

Additionally, poor or uneven contact of the electrode pad with the skin of a patient may unduly concentrate energy transfer during defibrillation into areas that exhibit good skin contact. Higher than usual current densities resulting from poor or uneven skin contact can cause skin burns. If the current is not delivered to a patient in the manner for which the electrode pad was designed, the resulting treatment delivered to the patient may be altered, compromising patient outcome.

Although highly hydrophilic hydrogels slow the gradual dehydration of stored, sealed electrodes, and also slow the gradual dehydration of electrodes on most exposed skin surfaces, the changes in mechanical and electrical properties over the long term exceed the tolerances in many medical applications. Moreover, highly hydrophilic gels have distinct disadvantages in applications requiring long-term, "wet" contact between electrode and skin, e.g., in a closed environment underneath a cast. In such wet environments, hydrophilic gels absorb water and/or sweat on the skin surface, causing swelling and even disintegration of the conductive pad.

U.S. Pat. No. 4,300,575 to Wilson discloses an air-permeable disposable electrode having a conductive silicone pad adapted to receive one end of an electrical lead from an active electrical instrument. The pad engages a permeable conductive element that is skin engageable through a permeable conductive adhesive coating. The permeable conductive element is formed primarily from karaya and carbon black so that the element can "breathe". The permeable conductive adhesive coating is likewise formed primarily from karaya so that the coating can also "breathe". A cover, also of air-permeable material, is provided with an adhesive on the inner side.

U.S. Pat. No. 4,300,575 states that it is essential that the conductive element and conductive adhesive coating provide an air-permeable covering to the skin of a patient so that the skin can "breathe" through the conductive element and adhesive coating. This enables the disposable electrode to be continuously used for relatively long periods of time on the order of a week or longer, whereas other disposable electrodes must be removed in a few days, at least from patients that have skin reactions resulting from contact of the skin with the disposable electrode.

As taught by U.S. Pat. No. 4,300,575, the permeable, conductive, adhesive coating interfacing with the skin of the patient electrode has no macroscopic exposed surface area (e.g., perforations), relying on microscopic, highly tortuous channels through which air molecules may permeate. Moreover, U.S. Pat. No. 4,300,575 fairly teaches away from a conductive interface layer having macroscopic exposed surface area, because such a configuration compromises the efficacy of the adhesive coating, and reduces the electrical contact area.

Moreover, the breatheability of the electrode is severely compromised by a conductive silicone pad, which serves to transfer electrical current from the electrical lead wire to the conductive element. The surface area of the silicone pad must be relatively large to convey the current. Typically, the silicone pad has a diameter of about 0.325 inches, and a thickness of about 0.020 inches. The skin lying underneath the relatively large area covered by the silicone pad is substantially sealed from air contact.

U.S. Pat. No. 4,367,755 to Bailey teaches an electrode for various stimulating applications, such as pain control. The electrode has a backing layer of conductive silicone rubber having a multiplicity of perforations. These perforations, preferably in the form of a rectangular grid pattern, are provided over the surface of the backing layer, with each perforation extending completely through the backing layer.

It should be appreciated that the perforations disclosed by U.S. Pat. No. 4,367,755 to Bailey are disposed solely in the backing layer. As illustrated and described, the conductive flexible pad interfacing with the skin, which is made of polymer gel or karaya gum, is continuous, and devoid of perforations. Like U.S. Pat. No. 4,300,575, U.S. Pat. No. 4,367,755 relies on microscopic, highly tortuous channels within the conductive flexible pad to enable the permeation of air molecules.

Although such a pad may be permeable to air molecules, the electrode taught by U.S. Pat. No. 4,367,755 to Bailey is, in many cases, inadequate for mass transport of sweat accumulating on the surface of the skin, through the pad, to the inside of the backing layer, and from the inside of the backing layer, via the perforations therein, to the atmosphere. The evaporation of water (in the sweat) is a function of the total amount of air diffusing from the environment to the skin surface, multiplied by the degree to which the air is unsaturated with respect to water vapor. Since the total flow of air reaching the skin surface is relatively small, the capacity to remove water at the skin surface is correspondingly low.

The thickness of the conductive, adhesive pad is a critical parameter in the delivery of air to the skin surface, and in the transport of water vapor from the skin surface out through the pad. With increasing thickness, the diffusion through the pad is reduced. The conductive, adhesive pad taught by U.S. Pat. No. 4,367,755 is of sufficient thickness and mechanical strength to withstand tensile and shear forces upon removal of the electrode from the patient, or movement and adjustment of the electrode upon the patient. These properties deleteriously influence the mass transport capability of the electrode, and hence, both the breatheability of the electrode and the ability of the electrode to transport water away from the underlying skin surface.

Moreover, the absorption of sweat into the conductive, adhesive pad serves to plug the channels or micropores within the pad, which further reduces both the breatheability of the electrode and the ability of the electrode to transport water away from the underlying skin surface.

Finally, it will be appreciated by one skilled in the field of mass transfer that the diffusion of air from the environment into the pad, and the diffusion, from the pad, of air containing moisture from the skin surface is impeded by the tortuosity of the diffusion path. As noted by Charles N. Satterfield in "Heterogeneous Catalysis in Practice" (McGraw-Hill, Inc., 1980, p. 336), "the length of the tortuous diffusion path in real pores is greater than the distance along a straight line in the mean direction of diffusion. Moreover, the channels through which diffusion occurs are of irregular shape and of varying cross section; constructions offer resistances that are not offset by the enlargements."

Satterfield further articulates that "if the gas density is low or if the pores are quite small, or both, the molecules collide with the pore wall much more frequently than with each other . . . . The gas flux is reduced by the wall 'resistance'". Hence, the prior art electrodes, in which relatively thick pads contact the skin surface, and in which the pad materials have characteristically small pores and high tortuosity factors, are generally incapable of providing sustained mechanical and electrical performance over long-term use of two weeks or more.

It will be appreciated that U.S. Pat. No. 4,367,755, like U.S. Pat. No. 4,300,575, teaches away from a conductive interface layer having macroscopic exposed surface area, because such a configuration compromises the efficacy of the adhesive coating, reduces the electrical contact area, and reduces the mechanical strength to withstand tensile and shear forces upon removal of the electrode from the patient, which is the main inventive thrust of U.S. Pat. No. 4,300, 575.

Furthermore, the stagnant conditions underneath a cast, coupled with the extremely long duration in which the cast encompasses or covers the skin surface (typically 3–10 weeks), render the above-described electrodes even more inadequate for transporting sweat accumulated on the surface of the skin, through the various conductive and adhesive pads, to the atmosphere. These stagnant conditions accelerate the process in which the above-described electrodes swell due to water absorption, lose their form, and move out of the proper position for transmitting the electrical signals.

The need for surface electrodes suitable for long-term electrical function is long-standing. Such surface electrodes are needed for receiving various kinds of electrical signals transmitted from within the body, and for delivering an electrical signal to the body, as in the case of electrical stimulation of muscle and/or bone tissue covered by a cast.

It would be highly advantageous, therefore, to have a surface electrode having sustained mechanical, physical and electrical performance over long-term storage and use, so as to enable transcutaneous electrical communication in a safe, comfortable, reliable, and effective manner, even under difficult topical and ambient conditions.

SUMMARY OF THE INVENTION

The present invention is a surface electrode for transcutaneous electrical communication, the electrode providing sustained mechanical and electrical performance over long-term use.

According to the teachings of the present invention there is provided a surface electrode for long-term electrical communication with a skin surface of a patient, the surface electrode including: (a) a highly-conductive foil, for operatively connecting to a power source, for communication of an electrical signal between the highly-conductive foil and the skin surface of the patient, and (b) a securing arrangement for securing the highly-conductive foil to the skin surface, wherein the highly-conductive foil has a plurality of macroscopic air-permeable regions for fluid communication of air with the skin surface, and wherein the plurality of macroscopic air-permeable regions has a first surface area, the foil has a second surface area, and a ratio of the first surface area to the second surface area is at least 0.1.

According to further features in the described preferred embodiments, the foil has an impedance of less than about 6 ohms.

According to still further features in the described preferred embodiments, the foil is designed and configured for directly contacting the skin surface.

According to still further features in the described preferred embodiments, the foil is designed and configured for directly contacting an ultra-thin, at least partially-conductive material disposed on the skin surface, the ultra-thin material having a thickness of less than 0.10 mm.

According to still further features in the described preferred embodiments, the surface electrode further includes: (c) an at least partially-conductive surface layer, operatively connected to the foil, for contacting with the skin surface of the patient.

According to still further features in the described preferred embodiments, the at least partially-conductive surface layer has a thickness of less than 0.5 mm, preferably less than 0.25 mm, more preferably, less than 0.20 mm, still more preferably, less than 0.10 mm.

According to still further features in the described preferred embodiments, the at least partially-conductive surface layer has a thickness of up to 0.05 mm.

According to still further features in the described preferred embodiments, the highly-conductive foil is for connecting to the power source so as to communicate the electrical signal to the skin surface of the patient.

According to still further features in the described preferred embodiments, the highly-conductive foil is for receiving the electrical signal via the skin surface of the patient.

According to still further features in the described preferred embodiments, the at least partially-conductive surface layer is a flexible surface layer.

According to still further features in the described preferred embodiments, the surface electrode further includes: (c) an at least partially-conductive surface layer, operatively connected to the foil, for directly contacting with the skin surface of the patient.

According to still further features in the described preferred embodiments, the at least partially-conductive surface layer is sufficiently pliable, such that when applied to the skin surface, the at least partially-conductive surface layer penetrates and at least partially fills pores in the skin surface.

According to still further features in the described preferred embodiments, the securing arrangement includes an adhesive bandage, operatively connected to the foil, for bonding the surface electrode to skin tissue surrounding the skin surface through which the electrical signal passes.

According to still further features in the described preferred embodiments, the foil is a metal foil.

According to still further features in the described preferred embodiments, the metal is selected from the group of metals consisting of gold and platinum.

According to still further features in the described preferred embodiments, the foil is bio-compatible.

According to still further features in the described preferred embodiments, the at least partially-conductive surface layer includes a conductive gel.

According to still further features in the described preferred embodiments, the at least partially-conductive surface layer includes an artificial skin.

According to still further features in the described preferred embodiments, the artificial skin includes a polymer membrane.

According to still further features in the described preferred embodiments, the artificial skin includes a dermal layer.

According to still further features in the described preferred embodiments, the electrical signal is characterized by a signal intensity, form, and distribution, wherein an impedance of the at least partially-conductive surface layer is sufficiently low such that the intensity, form, and distribution of the electrical signal are substantially unaffected by absorption of sweat into the layer.

According to still further features in the described preferred embodiments, the electrical signal is characterized by a signal intensity, form, and distribution, wherein an impedance of the at least partially-conductive surface layer is sufficiently low such that the intensity, form, and distribution of the electrical signal are substantially unaffected by a partial deterioration of the surface layer.

According to still further features in the described preferred embodiments, the ratio is at least 0.2, preferably, at least 0.25, and most preferably, at least 0.30 and less than 0.80.

According to still further features in the described preferred embodiments, the highly-conductive foil is for directly connecting to a lead wire of the power source.

According to still further features in the described preferred embodiments, each of the macroscopic air-permeable regions has a contiguous surface area of at least 1.0 square millimeter.

According to still further features in the described preferred embodiments, the artificial skin includes a material selected from the group consisting of a nylon matrix, gelatin, polyether, polyester, silicone, polytetrafluoroethylene (Teflon®), poly-L-lactide, cellulose, and collagen-based copolymer.

According to still further features in the described preferred embodiments, the artificial skin includes a bi-layer membrane.

According to still further features in the described preferred embodiments, the adhesive bandage, substantially alone, is for bonding the surface electrode to skin in vicinity of the skin surface.

According to still further features in the described preferred embodiments, the artificial skin includes polysiloxane.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 3a is a perspective, partially exploded view of the surface electrode of the present invention;

FIG. 3b is a schematic side view of the embodiment of FIG. 3a, and

DESCRIPTION OF THE PREFERRED EMBODIMENTS

The present invention is a surface electrode for transcutaneous electrical communication, the electrode providing sustained mechanical and electrical performance over long-term use.

The principles and operation of the surface electrode according to the present invention may be better understood with reference to the drawings and the accompanying description.

Before explaining at least one embodiment of the invention in detail, it is to be understood that the invention is not limited in its application to the details of construction and the arrangement of the components set forth in the following description or illustrated in the drawing. The invention is capable of other embodiments or of being practiced or carried out in various ways. Also, it is to be understood that the phraseology and terminology employed herein is for the purpose of description and should not be regarded as limiting.

There are several known devices for electrical stimulation of injured tissue situated underneath a cast, including U.S. Pat. Nos. 4,398,545, 4,574,809, 4,998,532, and 6,321,119, and U.S. Patent Application No. 20020016618, all of which are incorporated by reference for all purposes, as if fully set forth herein.

Figure 1A:
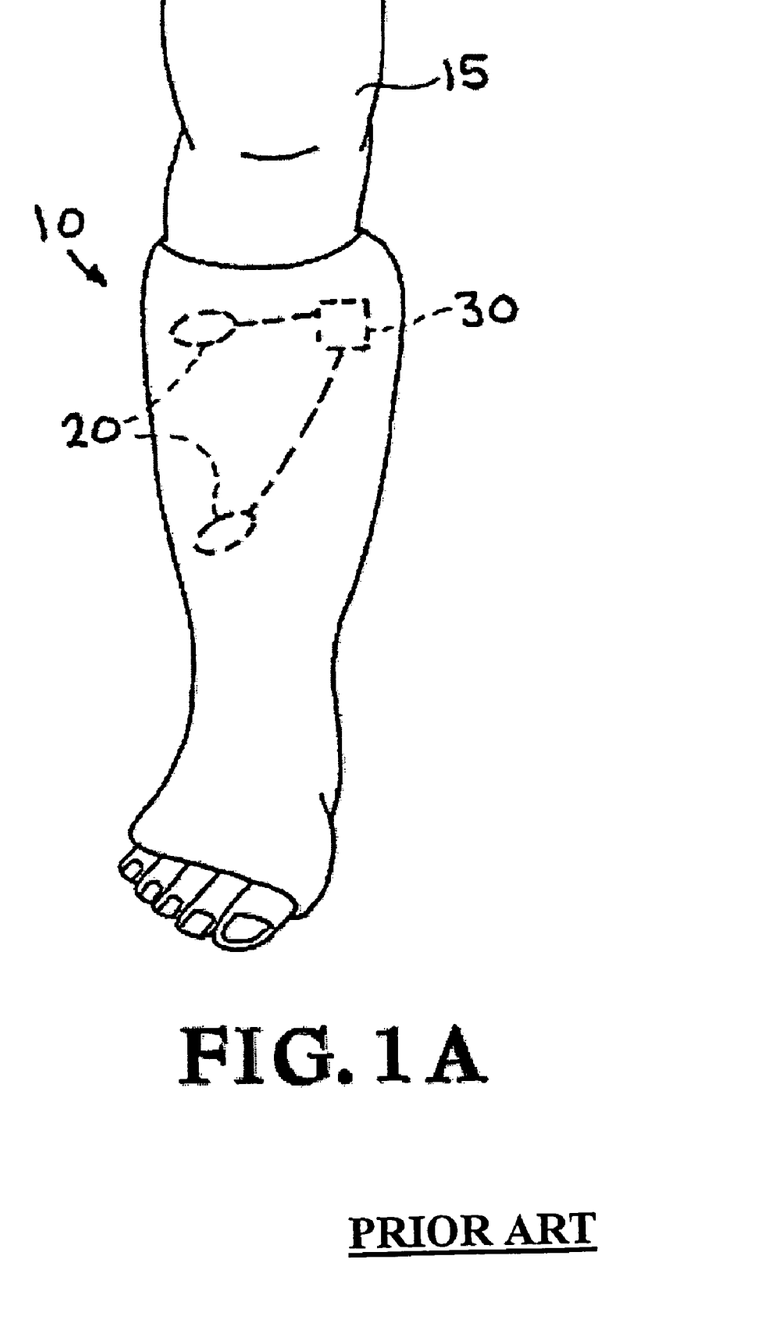
FIG. 1 shows a leg with a cast having an integrated muscle stimulation system, as disclosed in U.S. Patent Application No. 20020016618 to Da Silva et al.

By way of example, U.S. Patent Application No. 20020016618, to Da Silva, et al., teaches a device that allows electrical stimulation to an anatomical site covered by a cast. FIG. 1 shows the key components of this integrated cast and muscle stimulation device of the prior art, as the device would be used for a lower leg fracture. The cast 10 is molded around the lower leg 15 to immobilize the fracture. Replaceable electrodes 20 are positioned over superficial aspects of the peripheral nerves innervating the musculature surrounding the fracture site. An electrical stimulation unit 30 applies voltage pulses to the electrodes through buried electrical conductors (not shown).

The electrode port structure allows the placement of both an electrode module and a restraint module. In order to prevent skin from herniating into the port, either an electrode module or restraint module must be disposed within the port at all times.

Figure 2A:
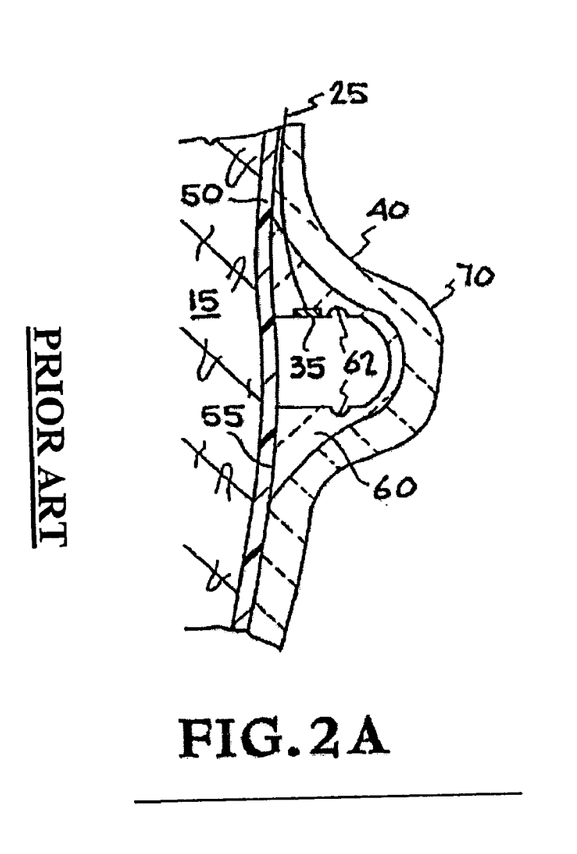
FIGS. 2A and 2B illustrate cross sectional view of the custom integration of the prior art port of FIG. 1 into the cast.
Figure 2B:
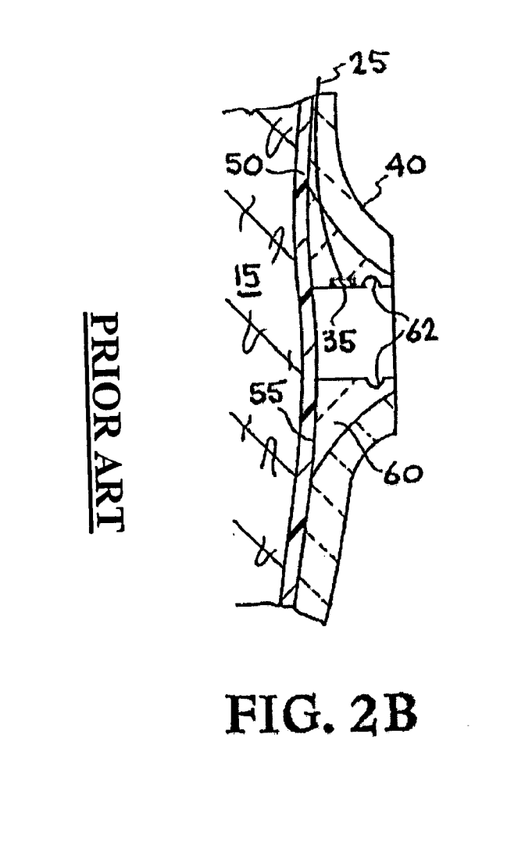

The replaceable electrodes 20 are inserted into a prepared port that is placed within the cast during the cast building phase. FIGS. 2A and 2B illustrate embodiments of how the port is integrated into the cast. First, the physician winds a layer of soft material 50 (e.g., cotton, foam, etc.) around the skin (e.g., lower leg 15) covering the broken bone. A special port structure 60 is then placed at the appropriate anatomical site for stimulation. The bottom surface of the lower section 55 could be adhesive to prevent the port structure from moving. The physician next applies the cast outer layers 40 that cover the port structure 60 and form a raised region 70 (FIG. 2A). The electrical conductor 25 connects to a conductive pad 35 that is exposed at the internal surface of the port. An indentation 62 is used to capture the electrode or restraint module. After the cast has dried and is rigid, a special saw is used to cut out the raised region producing a port as shown in FIG. 2B. The soft material 50 within the port structure can then be removed to expose the skin. The upper surface of the lower section 55 can be treated and coated with a primer to ensure bonding with the cast outer coat 40.

The port for the replaceable electrodes complicates the device in several respects. In addition to the additional equipment and fabrication requirements, the cast is intimately integrated with the muscle stimulation device. Consequently, the cost of the specialized cast is correspondingly high, and there are additional costs and procedures associated with the additional inventory requirements.

The device disclosed by U.S. Patent Application No. 20020016618, filed on May 10, 2001, employs replaceable electrodes, because there is no known surface electrode characterized by sustained mechanical and electrical performance both during long-term storage and during intimate contact with human skin over the course of several weeks, and more particularly, under the difficult topical conditions underneath a cast. While the electrodes taught by U.S. Pat. Nos. 4,300,575, and 4,367,755 were known in the art for close to 20 years prior to the filing of U.S. Patent Application No. 20020016618, these electrodes do not have the requisite combination of mechanical, physical and electrical properties for this function.

By sharp contrast, the surface electrode of the present invention provides the requisite sustained mechanical, physical and electrical properties during long-term storage and during intimate contact with human skin over the course of several weeks, even in the humid and saline environment underneath a cast.

Figures 3A, 3B:
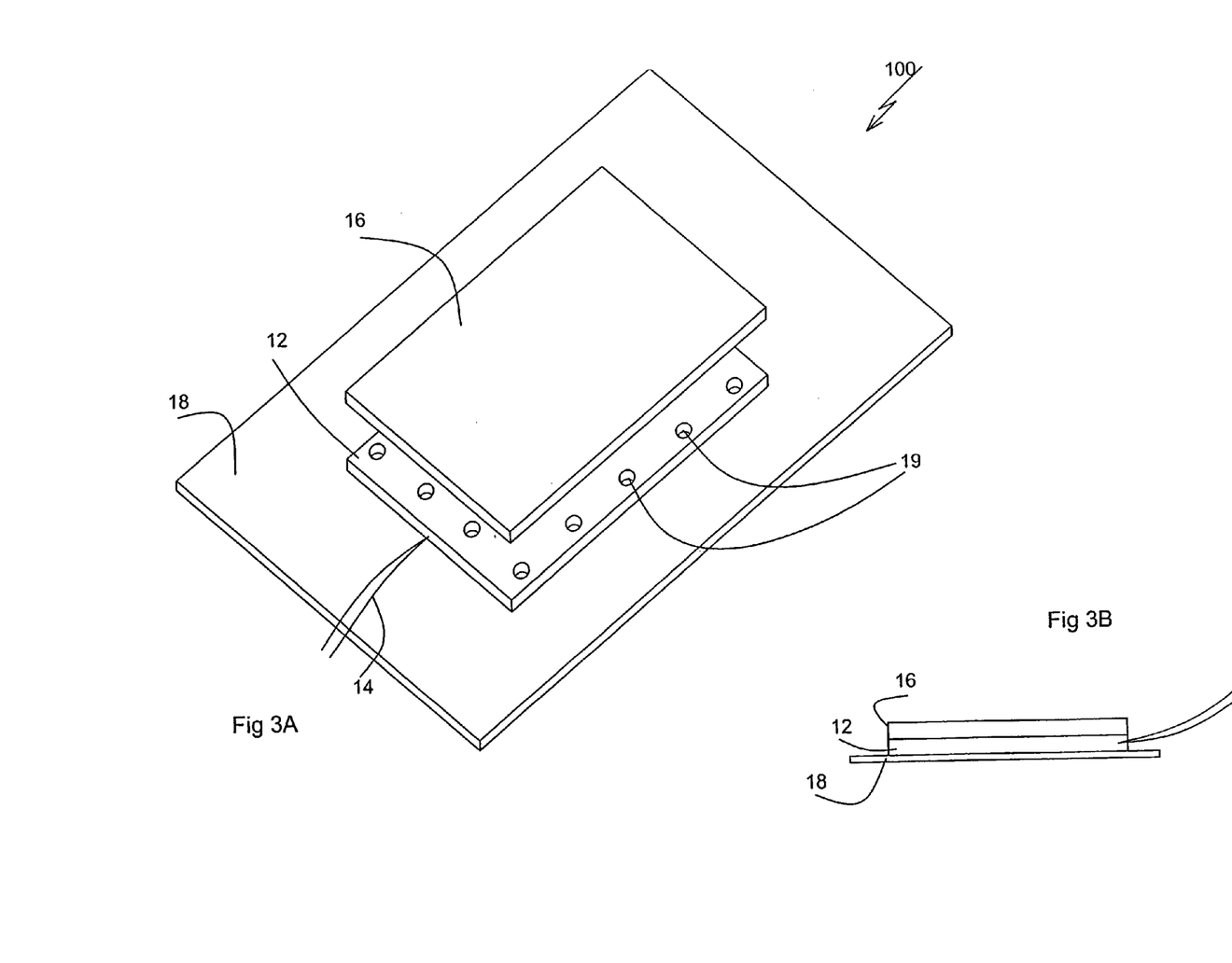

A perspective, partially exploded view of the surface electrode 100 of the present invention is provided in FIG. 3A. Surface electrode 100 includes a metal foil 112, for receiving an electrical signal from a power source or signal generator (not shown) via a conducting wire 114.

Preferably, as illustrated in FIGS. 3A and 3B, an adhesive bandage 118 is attached to a backside of metal foil 112, so as to cover and insulate metal foil 112—physically and electrically—with respect to the environment. It is generally preferable for bandage 118 to extend past the perimeter of both metal foil 112 and surface layer 116 in all directions, such that surface electrode 100 is adhesively connected to the skin surface, in all directions, by means of adhesive bandage 18.

It will be appreciated that various alternative constructions and dispositions of adhesive bandage 118 will be evident to one skilled in the art. Moreover, adhesive bandage 118 is a preferred example of a securing bandage or any another securing mechanism for fixing surface electrode 100 to the skin of the user.

Metal foil 112 is perforated to form macroscopic air-permeable regions 119, which enable surface electrode 100 to breathe. At least 10% of the surface area of metal foil 112 should consist of macroscopic air-permeable regions 119, preferably distributed evenly over the surface area of metal foil 112. Preferably, at least 20% of the surface area of the metal foil should consist of macroscopic air-permeable regions, even more preferably, 25% of the surface area, and most preferably, between about 30% and about 80% of the surface area.

As used herein in the specification and in the claims section that follows, the term "macroscopic", with respect to an air-permeable region and the like, refers to a contiguous surface area of at least 0.25 square millimeters. In many cases, it is advantageous for such macroscopic, air-permeable regions to have a contiguous surface area of at least 0.5 square millimeters, at least 1 square millimeter, or at least 2.5 square millimeters. When the metal foil has a mesh structure, for example, each macroscopic, air-permeable region may have a contiguous surface area of at least 10 square millimeters. As used herein in the specification and in the claims section that follows, the term "surface area", with respect to such an air-permeable region, refers to the surface area on the face of the foil that is for facing the skin surface.

The closest prior art teaches away from the use of metallic components in the surface electrode. For example, U.S. Pat. No. 4,300,575 to Wilson discloses, in the Abstract, an air-permeable surface electrode that is non-metallic and non-ionic. It is further articulated that "since the electrode is non-metallic and non-ionic, the danger of incorporation of metals into the body is substantially eliminated."

Metal foil 112 preferably includes at least one metal having good electrical conductivity along with various biocompatible and anti-microbial properties. In addition, metal foil 112 is preferably of a composition that is substantially inert with respect to the surface of the skin, such that no metals are incorporated into the body. Such metals include gold and platinum. It will be appreciated by those skilled in the art that various known metals and alloys have these properties, i.e., good electrical conductivity, biocompatibility, and inert behavior with respect to the surface of the skin and with respect to microorganisms.

As used herein in the specification and in the claims section that follows, the term "foil" is meant to include various mats, grids, screens, and the like.

As used herein in the specification and in the claims section that follows, the term "highly-conductive", with respect to a foil, refers to a foil having an impedance of about 0–10 ohms.

Preferably, metal foil layer 112, as characterized hereinabove, directly engages conducting lead wire 114, obviating the need for the silicone pad 11 of U.S. Pat. No. 4,300,575 to Wilson, which engages the electrical lead wire and distributes the current to conductive element 12. Similarly, metal foil 112 obviates the need for the raised protuberance 103 having a slot 104 for receipt of an electrical lead, as disclosed by U.S. Pat. No. 4,367,755 to Bailey.

Both the silicone pad 11 of U.S. Pat. No. 4,300,575 and the raised protuberance 103 of U.S. Pat. No. 4,367,755 are detrimental to the object of the surface electrode of the present invention, i.e., a surface electrode for transcutaneous electrical communication in a safe, comfortable, reliable, and effective manner. According to the teachings of the prior art, the current distributor (e.g., raised protuberance 103) does not allow the underlying skin to breathe. By sharp contrast, perforated, highly-conductive metal foil 112 of the present invention needs no current distributor, and is preferably connected directly to conducting lead wire 114.

As used herein in the specification and in the claims section that follows, the terms "directly engaged", "directly connected", and the like, with regard to metal foil layer 112, refer to an electrical connection between lead wire 114 and metal foil layer 112, without a current distributor therebetween.

According to a preferred embodiment of the present invention, a thin, at least partially-conductive surface layer 116 is attached to metal foil 112, so as to be disposed between metal foil 112 and a skin surface 121 of the patient (skin surface shown in FIG. 3B). In a preferred embodiment, surface layer 116 is made of a hydrophilic gel. The thickness of the hydrophilic gel in surface layer 116 is preferably less than 0.25 mm, more preferably, less than 0.20 mm, more preferably, less than 0.10 mm and most preferably, less than about 0.05 mm. The primary function of partially-conductive surface layer 116 is to fill the pores 123 on skin surface 121, so as to further reduce the impedance of the current flowing between the electrode and skin surface 121 (in either direction).

The electrical signal received via conducting wires 114 and metal foil layer 112 is delivered to the skin surface of the patient through surface layer 116. The partially-conductive properties of surface layer 116, along with the extremely small thickness, result in a low and even impedance between metal foil layer 112 and skin surface 121. Perhaps more significantly, the impedance between metal foil 112 and skin surface 121 is so low that the absorption of water and/or sweat, as well as distortion or partial deterioration of surface layer 116, do not significantly contribute to changes in the intensity, form, and distribution of the electrical signal delivered to the skin surface.

It must be emphasized that the present invention substantially decouples the functions of surface layer 116—adhesion and impedance reduction—as taught by the prior art. In the surface electrode of the present invention, the thickness of surface layer 116 is extremely small, so as to achieve the various electrical advantages described hereinabove. Consequently, the adhesive properties of surface layer 116 are compromised. Hence, surface electrode 100 is set for securing to the skin surface by means of adhesive bandage 118.

As used herein in the specification and in the claims section that follows, the term "substantially alone", and the like, with regard to the securing or the adhesion of the electrode to the skin surface, refer to a securing or an adhesion in which surface layer 116 contributes less than 20% of the total securing or adhesive force, such that at least 80% of the securing or adhesive force is provided by adhesive bandage 118.

According to another preferred embodiment of the present invention, surface layer 116 includes artificial skin. Artificial skin, in many present-day embodiments, is a combination of (human) skin cells and biodegradable polymers. A three-dimensional polymer matrix acts as a template or scaffolding on which the dermal cells grow. The polymer matrix provides a proper environment for dermal cell growth, and also gives the skin shape. The matrix is preferably dual-layered, so that the artificial skin can function much like real human skin. The underlayer is porous and designed to allow the ingrowth of human dermal cells. The outer layer is entirely synthetic and designed as a barrier against infection, water loss, and ultraviolet light. Typically, human dermal cells taken from neonatal foreskin are seeded onto the polymer matrix. The cells adhere to the matrix and are then allowed to incubate for several weeks. During this time, the cells multiply and organize themselves into functioning tissue.

Artificial skin is used as an interactive bandage to cover the wound until real skin grafts can be used to cover the wound. The artificial skin interacts with the body tissue to promote healing. Polymers used in artificial skin must be biocompatible, so that the body does not reject the tissue.

There are several products that are currently approved as temporary, interactive bandages. Advanced Tissue Sciences in La Jolla, Calif. has developed "Dermagraft-TC", an artificial skin made of a polymer membrane seeded with human cells. "Dermagraft-TC" is grown on a nylon mesh and then frozen. Freezing kills the cells, but leaves the tissue matrix and cell growth factors intact. This promotes growth of tissue around the wound. Integra Life Sciences has developed "Integra Artificial Skin", a product made of a dermal layer and a synthetic polysiloxane epidermal layer. In this case, the dermal layer interacts with the cells of the patient. Another product currently in use is "Original Biobrane", a bandaging product, which consists of a nylon matrix covered with a gelatin that promotes clotting factors in the wound.

Other biodegradable polymeric matrices for use in artificial skin include polyether/polyester copolymer, silicone interwoven with polytetrafluoroethylene (Teflon®), poly-L-lactide, cellulose, and collagen glycosamino glycan copolymers. It has been found to be advantageous to combine various copolymers made of both natural and synthetic components.

Figure 4:
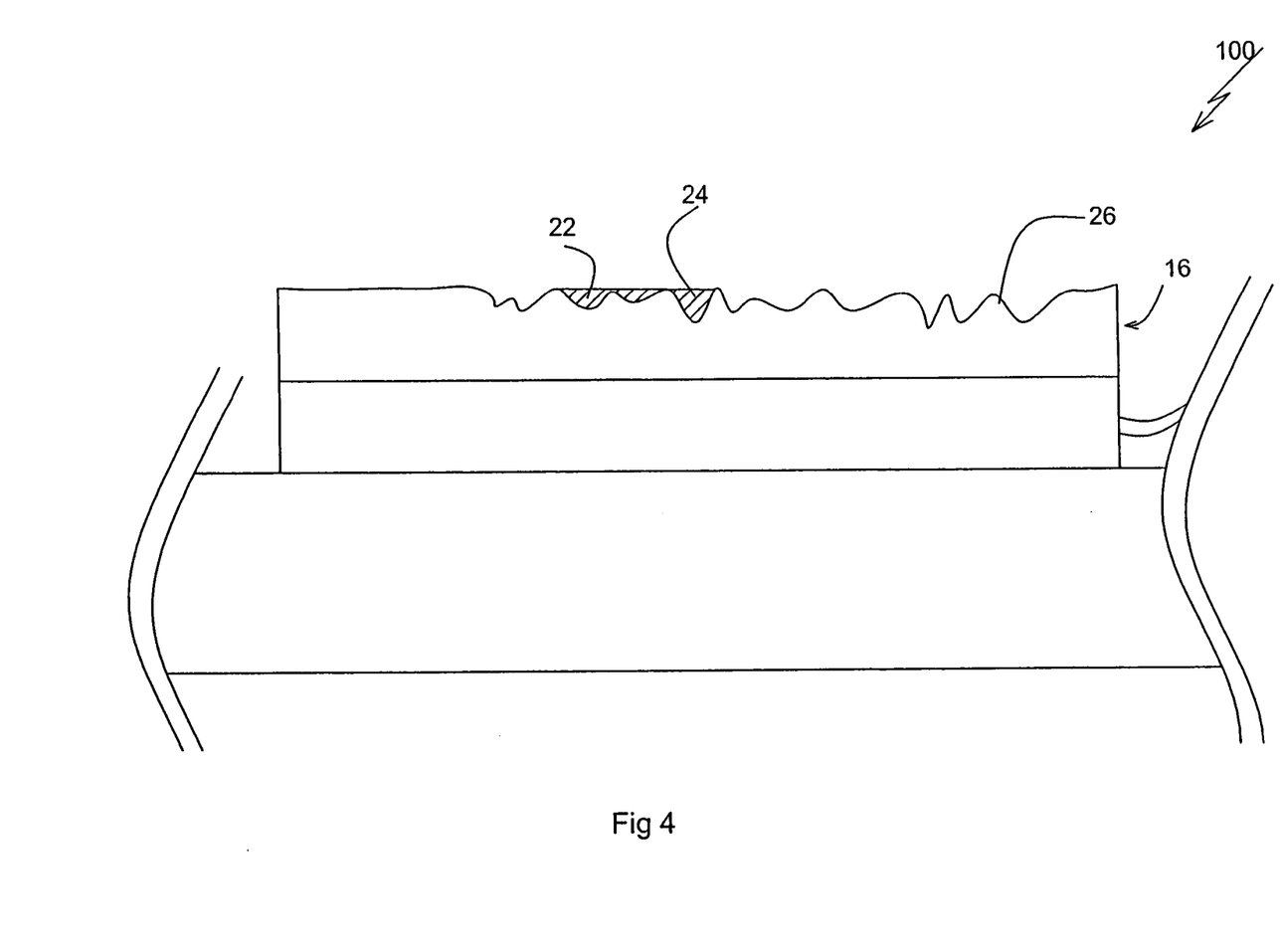
FIG. 4 is a schematic side view of another preferred embodiment, in which the surface layer of the electrode includes artificial skin and a conductive gel.

Surface layer 116 can consist entirely of artificial skin, or alternatively, artificial skin can be incorporated within surface layer 116. In one preferred embodiment, illustrated in FIG. 4, an at least partially conductive gel 122 is applied to surface layer 116 such that at least a portion of the surface 124 nearest the skin surface is at least partially coated with conductive gel 122. This improves the electrical contact with the skin surface, such that the impedance is low. In addition, the artificial skin 126 within layer 116 provides a high degree of breathability to surface electrode 200, and is generally well-tolerated by the skin surface. In the event that the tissue beneath surface electrode 200 has sustained some degree of damage, the artificial skin 126 within layer 116 can actually interact with the damaged skin surface so as to promote healing. Moreover, contact between the artificial skin 126 is much less likely to result in infection, relative to surface electrodes known in the art.

As used herein in the specification and in the claims section that follows, the term "artificial skin" is used generally to refer to an air-permeable matrix for placing against or near a skin surface of a patient, such that the skin surface can "breathe", even over continuous long-term use of two weeks and above.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A surface electrode for long-term electrical communication with a skin surface of a patient, the surface electrode comprising:
    (a) a highly-conductive foil, for operatively connecting to a power source, for communication of an electrical signal between said highly-conductive foil and the skin surface of the patient, and
    (b) a securing arrangement for securing said highly-conductive foil to the skin surface,
wherein said highly-conductive foil has a plurality of macroscopic air-permeable regions for fluid communication of air with the skin surface,
and wherein said plurality of macroscopic air-permeable regions has a first surface area, said foil has a second surface area, and a ratio of said first surface area to said second surface area is at least 0.1,
such that the surface electrode is a breathable surface electrode.

2. The surface electrode of claim 1, said foil having a first surface for disposing towards the skin surface and a second surface for disposing away from the skin surface, towards an environment, said breathable electrode having a top surface for disposing towards said environment,
    wherein said plurality of macroscopic air-permeable regions is designed and configured such that with said breathable surface electrode disposed on the skin surface, air from said environment fluidly communicates with the skin surface, via said top surface, so as to achieve a breathing of said breathable surface electrode.

3. The surface electrode of claim 2, wherein said securing arrangement includes a securing bandage, and wherein said securing bandage makes up at least a portion of said top surface.

4. The surface electrode of claim 2, wherein said securing bandage, substantially alone, is for bonding the surface electrode to skin in vicinity of the skin surface.

5. The surface electrode of claim 1, said foil designed and configured for directly contacting an ultra-thin, at least partially-conductive, material disposed on the skin surface, said ultra-thin material having a thickness of less than 0.10 mm.

6. The surface electrode of claim 1, further comprising:
    (c) an at least partially-conductive, breathable surface layer, operatively connected to said foil, for contacting with the skin surface of the patient, such that when disposed on the skin surface, the skin surface breathes via said breathable surface layer.

7. The surface electrode of claim 6, wherein said at least partially-conductive surface layer has a thickness of less than 0.20 mm.

8. The surface electrode of claim 6, wherein said at least partially-conductive surface layer has a thickness of less than 0.10 mm.

9. The surface electrode of claim 6, wherein said at least partially-conductive surface layer has a thickness of up to 0.05 mm.

10. The surface electrode of claim 6, wherein said highly-conductive foil is for connecting to said power source so as to communicate said electrical signal to the skin surface of the patient.

11. The surface electrode of claim 4, wherein said highly-conductive foil is for receiving said electrical signal via the skin surface of the patient.

12. The surface electrode of claim 4, wherein said at least partially-conductive surface layer is a substantially continuous surface layer.

13. The surface electrode of claim 4, wherein said at least partially-conductive surface layer includes an artificial skin.

14. The surface electrode of claim 13, wherein said artificial skin includes a polymer membrane.

15. The surface electrode of claim 4, wherein said at least partially-conductive, breathable surface layer includes a hydrogel.

16. The surface electrode of claim 15, wherein said breathable surface layer has a thickness of less than 0.05 mm.

17. The surface electrode of claim 16, wherein said artificial skin includes a dermal layer.

18. The surface electrode of claim 4, wherein said electrical signal is characterized by a signal intensity, form, and distribution, and wherein an impedance of said at least partially-conductive surface layer is sufficiently low such that said intensity, said form, and said distribution of said electrical signal are substantially unaffected by absorption of sweat into said layer.

19. The surface electrode of claim 4, wherein said electrical signal is characterized by a signal intensity, form, and distribution, and wherein an impedance of said at least partially-conductive surface layer is sufficiently low such that said intensity, said form, and said distribution of said electrical signal are substantially unaffected by a partial deterioration of said surface layer.

20. The surface electrode of claim 4, wherein said ratio is at least 0.2.

21. The surface electrode of claim 1, wherein said foil is a metal foil.

22. The surface electrode of claim 21, wherein said metal is selected from the group of metals consisting of gold and platinum.

23. The surface electrode of claim 1, wherein said ratio is at least 0.2.

24. The surface electrode of claim 1, wherein said ratio is at least 0.25.

25. The surface electrode of claim 1, wherein said ratio is at least 0.30 and less than 0.80.

26. The surface electrode of claim 1, wherein each of said macroscopic air-permeable regions has a contiguous surface area of at least 1.0 square millimeter.

27. A breathable surface electrode for long-term contact and electrical communication with a skin surface of a patient, the surface electrode comprising:
   (a) a highly-conductive foil, for operatively connecting to a power source, for communication of an electrical signal between said highly-conductive foil and the skin surface of the patient, said highly-conductive foil having a plurality of macroscopic air-permeable regions;
   (b) a securing arrangement for securing said highly-conductive foil to the skin surface, and
   (c) a bandage, covering said foil, so as to form a top surface of the breathable surface electrode,
the surface electrode designed and configured such that when the surface electrode is in contact with the skin surface, said bandage and said plurality of macroscopic air-permeable regions enable a fluid communication of air with the skin surface, via said top surface of the surface electrode, such that the surface electrode is a breathable surface electrode.

28. The surface electrode of claim 27, wherein said plurality of macroscopic air-permeable regions enable said fluid communication of air with the skin surface, via said top surface of the surface electrode, such that the surface electrode remains breathable during continuous, long-term use of at least two weeks.

29. The surface electrode of claim 27, wherein the surface electrode is in contact with the skin surface underneath a cast, and wherein said plurality of macroscopic air-permeable regions enable said fluid communication of air with the skin surface, via said top surface of the surface electrode, such that the surface electrode remains breathable during continuous, long-term use of at least two weeks skin surface underneath said cast.

30. A method of applying a breathable surface electrode for long-term contact and electrical communication with a skin surface of a patient, the method comprising the steps of:
   (a) providing the breathable surface electrode, including:
      (i) a highly-conductive foil, for operatively connecting to a power source, for communication of an electrical signal between said highly-conductive foil and the skin surface of the patient, said highly-conductive foil having a plurality of macroscopic air-permeable regions;
      (ii) a securing arrangement for securing said highly-conductive foil to the skin surface, and
      (iii) a bandage, covering said foil, so as to form a top surface of the breathable surface electrode;
   (b) applying the breathable surface electrode to the skin surface of the patient, and
   (c) operating the breathable surface electrode so as to effect said communication of said electrical signal between said highly-conductive foil and the skin surface of the patient.

31. The method of claim 30, wherein said applying of the breathable surface electrode to the skin surface is effected continuously for a period of at least two weeks, and wherein the surface electrode remains breathable throughout said period.

32. The method of claim 31, wherein the skin surface of the patient is disposed underneath a cast.

* * * * *